US006574742B1

(12) United States Patent
Jamroga et al.

(10) Patent No.: US 6,574,742 B1
(45) Date of Patent: Jun. 3, 2003

(54) METHOD FOR STORING AND ACCESSING DIGITAL MEDICAL IMAGES

(75) Inventors: David Jamroga, Stamford, CT (US);
Richard J. Friswell, Somerville, MA (US); David S. Cook, Woodbridge, CT (US); Michael K. Patenaude, Wallingford, CT (US)

(73) Assignee: InSite One, LLC, Wallingford, CT (US)

(*) Notice: Subject to any disclaimer, the term of this patent is extended or adjusted under 35 U.S.C. 154(b) by 53 days.

(21) Appl. No.: 09/711,052

(22) Filed: Nov. 10, 2000

Related U.S. Application Data

(60) Provisional application No. 60/164,998, filed on Nov. 12, 1999.

(51) Int. Cl.[7] ................................................. G06F 1/12
(52) U.S. Cl. ......................... 713/400; 711/161; 705/2
(58) Field of Search .......................... 705/2, 3; 711/100, 711/117, 147, 161, 167; 707/500, 204, 513, 103, 514; 713/400

(56) References Cited

U.S. PATENT DOCUMENTS

| 5,301,105 | A |   | 4/1994  | Cummings          |
|-----------|---|---|---------|-------------------|
| 5,321,520 | A |   | 6/1994  | Inga et al.       |
| 5,790,668 | A |   | 8/1998  | Tomko             |
| 5,831,612 | A |   | 11/1998 | Stoval, III et al.|
| 5,857,967 | A |   | 1/1999  | Frid et al.       |
| 5,876,926 | A |   | 3/1999  | Beecham           |
| 5,950,632 | A |   | 9/1999  | Reber et al.      |
| 6,006,191 | A |   | 12/1999 | DiRienzo          |
| 6,049,821 | A | * | 4/2000  | Theriault et al. ........... 709/203 |
| 6,205,481 | B1| * | 3/2001  | Heddaya et al. ............ 709/226 |
| 6,260,021 | B1| * | 7/2001  | Wong et al. ................... 705/2 |
| 6,349,373 | B2| * | 2/2002  | Sitka et al. .................. 711/161 |

OTHER PUBLICATIONS

Wong, et al. A Hospital Integrated Framework for Multimodality Image Base Management, Systems, Man and Cybernetics, Part A, IEEE Transactions, vol. 26, Issue 4, Jul. 1996, pp. 455–469.*

Authentication of Digital Medical Images with Digital Signature Technology by Justin P. Smith, Mar. 1995, Computer Applications—pp. 771–774.

* cited by examiner

Primary Examiner—Richard Chilcot
Assistant Examiner—J Harle
(74) Attorney, Agent, or Firm—St. Onge Steward Johnston & Reens LLC

(57) ABSTRACT

A system for communication, storage, retrieval and delivery of information between the system and participating institutions and sites includes institution, warehouse and central servers sequentially receiving data from the participating institutions. The institution server is provided with an index stored in the institution server and constantly updated upon receiving new information. The central server has a long-term storage accessible from the warehouse server to provide the requested information to the participating institutions if this information is not found on either of the institution or warehouse servers.

65 Claims, 11 Drawing Sheets

METHOD FOR STORING AND ACCESSING DIGITAL MEDICAL IMAGES

This application claims the benefit of provisional application 60/164,998 filed Nov. 12, 1999.

FIELD OF THE INVENTION

The invention relates to a system for querying, storing, retrieving and delivering digital data and images, and more particularly, to a device and method for communicating the storage and retrieval transactions between the system and participating institutions and sites.

BACKGROUND OF THE INVENTION

A variety of systems have been developed for storing and retrieving digital data and images. With the advent of digital imaging and Picture Archiving and Communication Systems (PACS), the digital storage of medical images and data is becoming the norm. At the heart of all of this is the archive, the proper performance of which is key to the overall success of a PACS deployment. Much like the more traditional film library, the digital archive's essential function is to store, identify and protect image data—but with more versatility, like decreased costs, robust security and the long-term maintenance of data integrity.

In addition, hospitals, imaging centers, radiology departments and physician group practices throughout the country are exploring new technological tools in order to reduce "wait time" between diagnosis and treatment. Many institutions are looking towards film-less storage media as a means of improving efficiency, as well as, providing cost-effective solutions that address many of these demands.

The transition to film-less storage in the near future will allow all patient medical data, including radiological images, to be available instantly from any hospital workstation. This new digital world will enhance patient care, increased convenience, improve treatment cost-effectiveness and transform radiology processes.

Recent and upcoming legislation has forced the medical industry to move towards developing and implementing stricter standards dealing with the security of computer-based patient records. These standards require both data management and disaster recovery systems. In addition, many other industry and technologic forces are driving the need to streamline data processes and management capabilities.

The Digital Imaging and Communications in Medicine (DICOM) standard, developed by The American College of Radiology (ACR) and the National Electrical Manufacturers Association (NEMA), seeks to standardize the transferring of medical images and information between electronic devices by interconnecting medical imaging equipment and devices on computing networks. DICOM was initially developed to support interoperability and connectivity in radiology; however, the DICOM standard also supports many other modalities including ultrasound, X-ray and radiotherapy. DICOM supports the creation of files on removable media (such as optical disks or high-capacity magnetic tape), data structures for X-ray angiography and extended hard copy print management. The goal of DICOM is open architecture, which permits users to integrate imaging equipment from different manufacturers to support a range of modalities, as well as computer-radiography and digitized film radiographs.

Hospitals and radiology centers will sooner or later be faced with the need to transition from film-based technology to digital imaging, all while maintaining productivity in order to stay competitive in today's healthcare environment. Advances in technology, such as DVD storage, provides a method to store and access medical and radiological images.

The major legal force behind the need to transform the way the medical industry handles digital patient records is The Health Insurance Portability and Accountability Act of 1996 (HIPAA). This act mandates that standards be established to govern the privacy of electronically stored and transmitted health information. The basis behind the proposed rules is the need to assure patients that the confidentiality and privacy of healthcare information collected, maintained, used or transmitted electronically is secure. In carrying out this task, HIPAA requires that all healthcare organizations that maintain or transmit health information electronically establish and maintain reasonable and appropriate administrative, technical and physical safeguards to ensure the integrity, confidentiality and availability of the information. These safeguards must also protect the information against any reasonably anticipated threats or hazards to its security or integrity and protect it against unauthorized use or disclosure.

Measures must include:
- Administrative procedures to guard data integrity, confidentiality and availability;
- A contingency plan for responding to a system emergency, wherein the data backup plan should include a method for the retrieval of exact copies of information for a specific period of time, as well as, a process enabling an enterprise to restore any loss of data in the event of fire, natural disaster, vandalism or system failure; and
- Physical safeguards to guard data integrity, confidentiality and availability, including the protection of the physical computer system and related buildings.

In addition to the legal forces, demand for digital imaging is being driven by many industry factors. A few of the industry forces behind the digital movement are the desire to streamline; increase storage capacities; eliminate cine film; improve patient care; and enhance productivity by reducing image development, review and retrieval time.

Many hospitals and medical groups throughout the U.S. are storing medical information, including images, in a form that many consider "primitive". Nearly 90% of healthcare information is still stored on paper, and film is the predominant storage medium in radiology. Files in some institutions exist only in their original film form and are stored in remote locations. For older data, they may need to physically retrieve a case study from an off-site storage location, taking hours or even days. This age-old, inefficient process not only takes days to complete, but results in high storage costs and hampers quick diagnosis and intervention.

It is obvious that these facilities are faced with the need to modernize their processes and equipment. In fact, the rapid shift toward film-less digital radiology presents a growing need for hospitals and medical groups to modernize their entire radiological systems. This decision is being defined by the need to stay competitive, work more efficiently and provide state-of-the-art technology. But while the motivation is compelling, the transition to digital imaging is a difficult task requiring expensive equipment, management and training at a time when hospitals are faced with mounting pressure to increase efficiency and lower costs.

To keep up with changing technologies and to meet the storage needs that these files require, hospitals will need to either upgrade their current systems or change technologies completely. The systems and media needed to store the magnitude of data digital files require can be costly, especially over time. Tape storage systems can be upwards of $100,000 not including $150 per tape, plus the time required to manage the system. In addition, expanding the system over time results in costly upgrades for additional hardware.

With a limited number of options, the adoption of digital imaging technology within a hospital's radiology department has tended to focus on an enterprise-wide PACS solution—an information system that may include or interface to a Radiology Information System (RIS) and/or Hospital Information System (HIS). While a PACS reduces the costs of film-based imaging, the biggest challenge is the economical storage and archiving of data, which requires intensive internal management and can strain hospital IT resources.

The transition from film to digital imaging within the medical community is still in its early stages. Radiology departments are confronted with the need to convert to film-less technology in order to stay current with new diagnostic technologies, curb costs and stay competitive.

A film-less approach should mean both short-and long-term gains in quality and visualization without compromising image quality. Unlike film, digital image deterioration is less likely to occur over time with the use of a medium such as DVD or its equivalent. This will guaranty long-term gains.

The trend toward large PACS purchases by hospitals and imaging centers has recently been replaced by a digital conversion strategy that focuses on the acquisition of selected components of the system. This "mini-PACS" model relies on finding cost savings by "unbundling" the end-to-end product-driven proposal (with its disproportionate markups) and purchasing only those components that offer the radiology department the functionality that is needed.

Using this approach, it can be very beneficial to lease certain specialized services, such as long-term digital storage, on an as-needed basis. The invention offers an alternative to the digital image storage and retrieval component of an overall PACS with a specified term service contract. The open architecture that this model employs removes the burden of archival management from the extensive list of a facility's responsibilities. Both staff and financial resources can be freed up to focus on the department's primary mission—providing high quality clinical diagnostics.

This strategy provides hospitals with a solution that both maximizes capital and increases efficiency in the management of digital medical images. Thus, the medical facility can effectively address the challenge of increasing efficiency while decreasing expenditures. As a highly specialized and adaptable DICOM storage and retrieval warehouse, the invented solution provides speed, quality, security, flexibility, scalability, cost savings and expandability appropriate to each facility's needs.

Specifically, it enables hospitals to cost-effectively outsource the warehousing, storage and access of digital radiological images, allowing medical facilities to implement greater flexibility in budgeting procedures, so that needed capital can be redirected to areas key to quality patient care. By contracting for the archiving component separately, hospitals can save up to 30% of a PACS cost—not to mention future costs of upgrades, technical support and compliance with the newly defined confidentiality and privacy laws (DICOM and HIPAA).

Designed to optimize the storage and archiving of DICOM images for hospitals entering the new film-less digital medical imaging age, the invention offers service for both online and near line storage and access and offline archiving of DICOM images. The invention provides archiving and retrieval sessions with an offsite digital network where electronically protected digital images can be received "on demand" over the Internet, via a Virtual Private Network (VPN), or dedicated lines. All digital images are replicated, archived and stored at a third location offsite in warehouses. The additional layer of off-site redundancy also helps hospitals implement the legislative mandates to plan for disaster recovery.

The present invention provides a truly unique, scalable and affordably priced method for DICOM image storage management—and allows the invention to provide a solution that is faster, more secure and more cost-effective than a hospital could achieve on its own. Many off-the-shelf databases considered for in-house systems are neither efficient nor fast enough to handle large DICOM objects. Secondly, economies of scale are applied to amortize the advanced technology and resources required for the storage and archiving components including communications bandwidth, storage media, software and hardware, human and technical resources and system maintenance. Also, because of the physical nature of film, storage facilities today must be located in close proximity to the hospital site. Off-site and redundant storage of electronic media entails extra costs for personnel equipment and physical space. The invention's digital warehouses, RAID and DVD OR ITS EQUIVALENT systems design provides fail-safe disaster recovery and 24×7 monitoring in case of loss or failure of onsite images. Facility archives can grow with its department's conversion to PACS and increased use of digital modalities. With terabytes of virtual space, storage costs are controlled because customers are only buying the storage and archiving capacity they need at the time.

Permanent hardware purchases are expensive and prone to being overwhelmed by volume demands and obsolescence, particularly when dealing with the highly specialized requirements such as digital image storage. Given its reliance on sophisticated security layers, firewalls, bandwidth and technical support, closed-ended archival hardware is also expensive to staff and maintain. The invention provides an alternative solution to storage hardware ownership which is both sensible and cost effective.

SUMMARY OF THE INVENTION

Accordingly, it is the object of the invention to provide a communications, storage, retrieval and delivery device and method for use by participants which improves the speed, reliability and functionality of digital data and image storage, retrieval and delivery transactions.

Another object of the invention is to provide a communication device and method of the above character which is compatible with a plurality of radiology modalities, PACS, HIS, RIS, and compatible with DICOM standards.

Still another object of the invention is to provide a communication device and method of the above character which is compatible with HIPAA, and other Federal and State laws and regulations relating to medical patient record privacy and security standards.

A further object of the invention is to provide a communication device and method of the above character including one or more databases which are automatically accessed by a communication device.

Yet another object of the invention is to provide a communication device and method of the above character for automatically transmitting query, storage, retrieval, and delivery instructions from participant institutions.

Still a further object of the invention is to provide a communication device and method of the above character for automatically transmitting query, storage, retrieval, and delivery instructions to participant institutions.

Yet still another object of the invention is to provide a communication device and method of the above character where security control software is programmed to limit accessibility to the system.

Still a further object of the invention is to provide a communication device and method of the above character having software for remote monitoring of system devices and for updating device software and security control software.

Still another object of the invention is to provide a communication device and method of the above character where the system devices have access to the World Wide Web.

Still another object of the invention is to provide a communication device and method of the above character in which current and archived data and images are searchable by users at shared-access or remote locations.

Yet another object of the invention is to provide a communication device and method permitting real time access to stored or archived data and images from remote locations.

Yet another object of the invention is to provide a communication device and method of the above character permitting the tracking and reporting of participant transactions.

Still a further object of the invention is to provide a communication device and method of the above character for automatically applying digital signatures or message digests to transactions transmitted by participant institutions to the system devices.

These and other objects of the invention are achieved by provision of a digital data and image storage, retrieval and delivery communication device comprising a series of computer servers, storage devices and one or more databases for storing a plurality of query, storage, search and delivery information or instructions sets, a database receiver for receiving an identifier, a database searcher for searching the database, and a database transmitter for transmitting the retrieved instruction set corresponding to the identifier. The database preferably also includes a message generator for notifying participants of changes to the database.

The storage, retrieval and delivery communication device also includes a participant computer server transmitter device for communicating with the system devices located at the database storage facility. This device contains both a transmitter and receiver for receiving and outputting the retrieved, transmitted delivery instruction set and digital data and images. Most preferably, the communication delivery device are both receiver-transmitters for performing each other's functions and comprise input units for adding and changing delivery instruction sets on the database. The system communication device is more preferably an n-customer to 1 server (client/server) system. Each customer node is connected via a communications link (Internet, VPN, VAN, dialup, etc.) to the main database server system. This provides for independent customers and servers, and thus provides for the ability of both systems to work independently. The participant computer server transmitter device acts as a transaction cache and delivery device from participant medical devices and modalities, and provides communications between the participant and the database system computer server.

The one or more databases preferably also include a plurality of account information sets, which include participant storage delivery instruction sets specified by participant institution.

In other aspects, the invention comprises methods of operating the database or databases and the query, storage, retrieval and delivery communication devices. The invention and its particular features and advantages will become more apparent from the following detailed description considered with reference to the accompanying drawings.

DETAILED DESCRIPTION OF THE DRAWINGS

Figure 1:
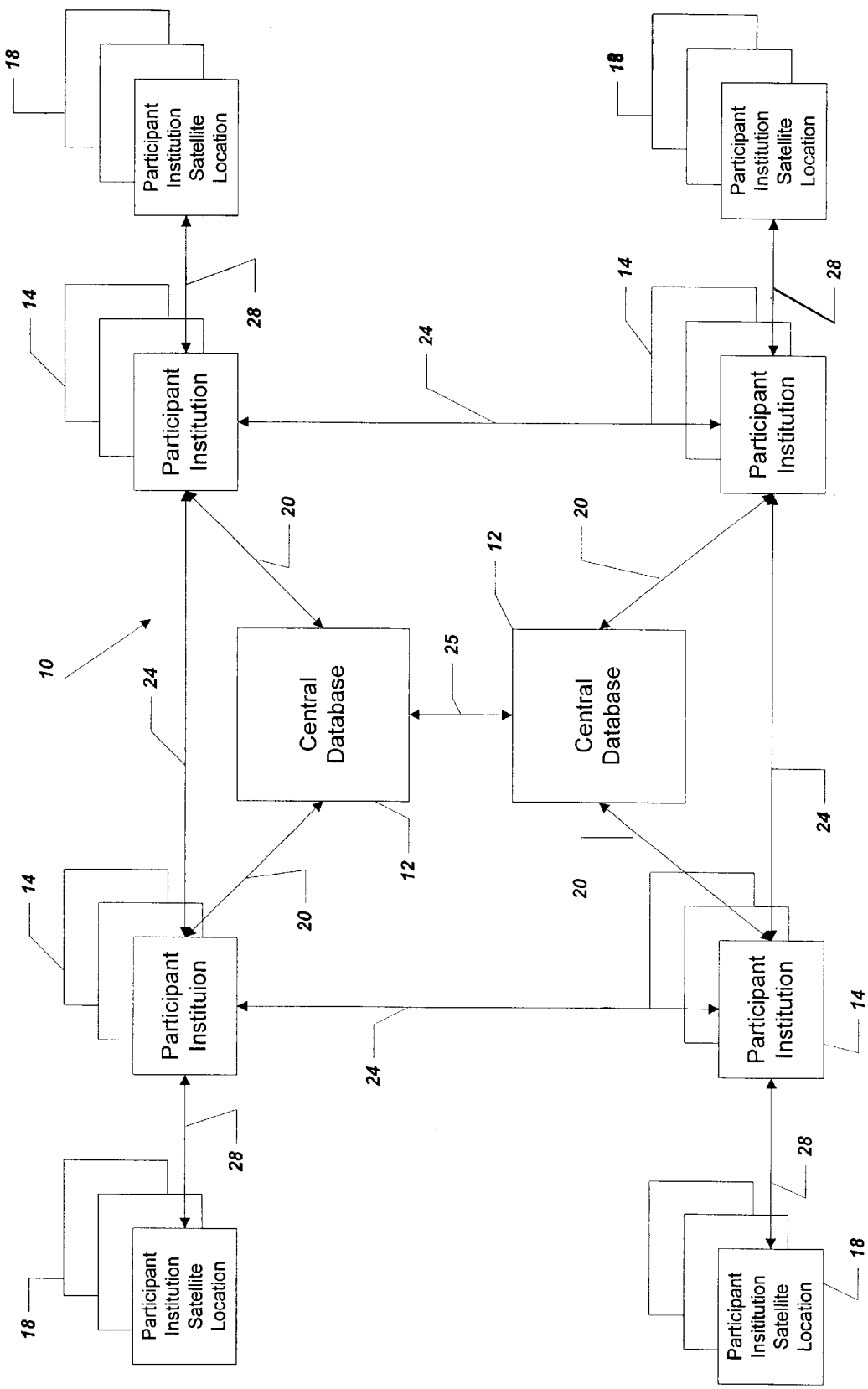
FIG. 1 is a block diagram of a communications device and method in accordance with the invention.

FIG. 1 is a block diagram of a system device and method 10, in accordance with the invention, for communicating query, storage, retrieval and delivery of digital data and images between the system device central databases 12 and participants such as myriad institutions 14, and institution satellite locations 18. By "digital data and images" is meant a plurality of DICOM or non-DICOM formatted bits and/or bytes of data stored or transmitted as a sequence of discrete symbols from a finite binary set represented using electronic or electromagnetic signals, and/or composed of pixels arranged in a rectangular array and/or other formats with a certain height and width possibly including color information, and all relevant information associated with the data or image, which includes both medical and non-medical images. By "participant institution" is meant hospitals, radiology group practices, physician group practices, medical imaging centers, and other healthcare facilities and organizations. By "participant satellite locations" is meant physician offices, clinics, diagnostic centers, and other medical and/or healthcare facilities associated with or participating with participant institutions.

Each line on FIG. 1 schematically depicts a communication link in method and device 10. The diagonal line or lines 20 represent communications links between participant institutions 14 and the central database 12 (or databases). These diagonal links 20 are discussed in more detail with reference to FIGS. 2 and 8. The vertical line 25 between the central databases 12 represents communication links utilized to transfer digital data and images between the various remotely located central databases 12. The horizontal and vertical lines 24 between participant institutions 14 represent communication links utilized to transfer digital data and images between the various institutional participants. These communications links are more preferably Internet connections, but may also include dedicated lines and VPN connections. Horizontal lines 28 between client institutions 14 and client satellite locations 18 represent communications links utilized to transfer digital data and images between institution participants 14 and their various satellite locations 18. These communications links are more preferably direct network connections, but may also include Internet connections, dedicated lines and VPN connections. Links 24 and 28 are discussed in more detail with reference to FIG. 12. The vertical line 25 between the central databases 12 represents a communication link between two or more central databases utilized to transfer digital data and images. Link 25 is discussed in more detail with reference to FIGS. 2 and 5.

Links 20–28 are communications lines, however, it is understood that dedicated wire or wireless links may also be used. It is understood that by "wire" is meant any physical connection, whether by optical fiber, coaxial cable, twisted pair or otherwise, and that by "wireless" is meant cellular, microwave, IR, laser or any other non-physical connection. In this regard, the participant institutions 14 and their satellite locations 18 each have computers, computer networks, modalities, terminals, input/output devises, transceivers or the like (not shown) for transmitting and receiving digital data and information, e.g. by modem, over the communication links.

Figure 2:
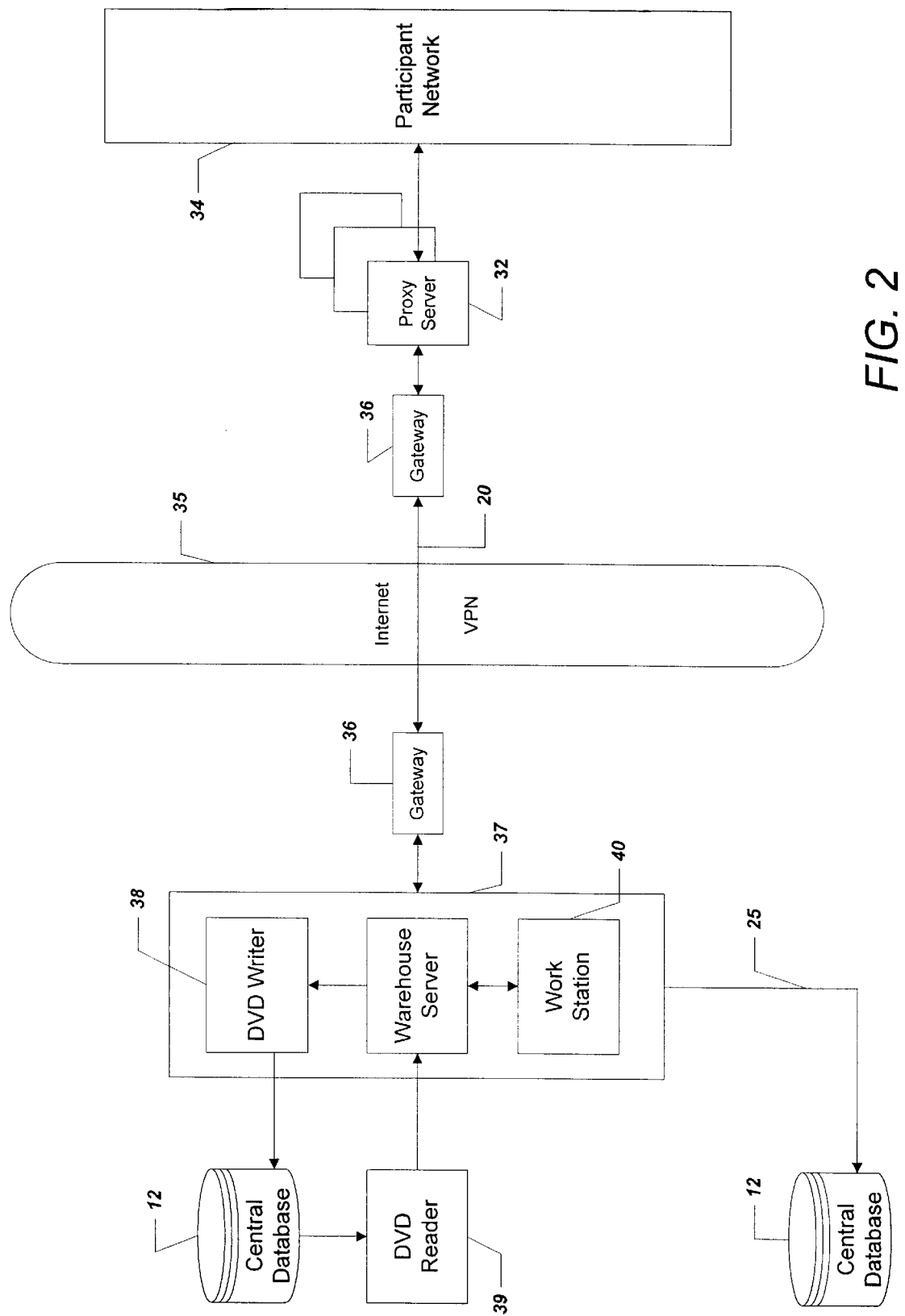
FIG. 2 is a block diagram of a database and communications device and method of FIG. 1.

Referring to FIG. 2, reference in this description to the participant institution, thus, includes the participants' system terminals, computer networks, and modalities, collectively called the "Participant Network". Each of these participant networks 34 is connected to the system device and method 10 via a proxy server 32. The proxy server is a computer server device, which acts as an intermediary between the participants network and modalities and the central database 12, and acts as a transaction cache and delivery device from participant medical devices and modalities, and provides communications between the participant and the database system computer server. Each of these proxy servers includes a unique name or acronym identifying it as the transmitter or recipient of messages or data over the system, and each proxy server includes application software written in C or C++, or other languages, for maintaining and operating central database 12 as described with reference to FIGS. 2, 5, 6, 7, 8, and 10, and for establishing communications links 20 as described with reference to FIGS. 1, 2, 5, 6, 7, 8 and 10. The proxy servers 32 are typically rack mounted servers preferably having system requirements of one 27U Rack or equivalent, with Linux version 6.2 or newer operating system, one HP Lpr Netserver or equivalent, a 500 Mhz Pentium III processor or greater, 1 GB of random access memory, Keyboard, Mouse, one or two 300 GB, more or less, RAID-5 disk array, a VGA color monitor, and an APC 1400 rack mount UPS. These proxy server are linked directly to the participant's computer network with a direct connection to the participants' imaging modalities. Further, a particular participant may have multiple modalities, PCs, or viewing stations connected to the proxy server through the participants network so that steps of device and method 10 may be carried out by different persons at the particular participant simultaneously.

Figure 5:
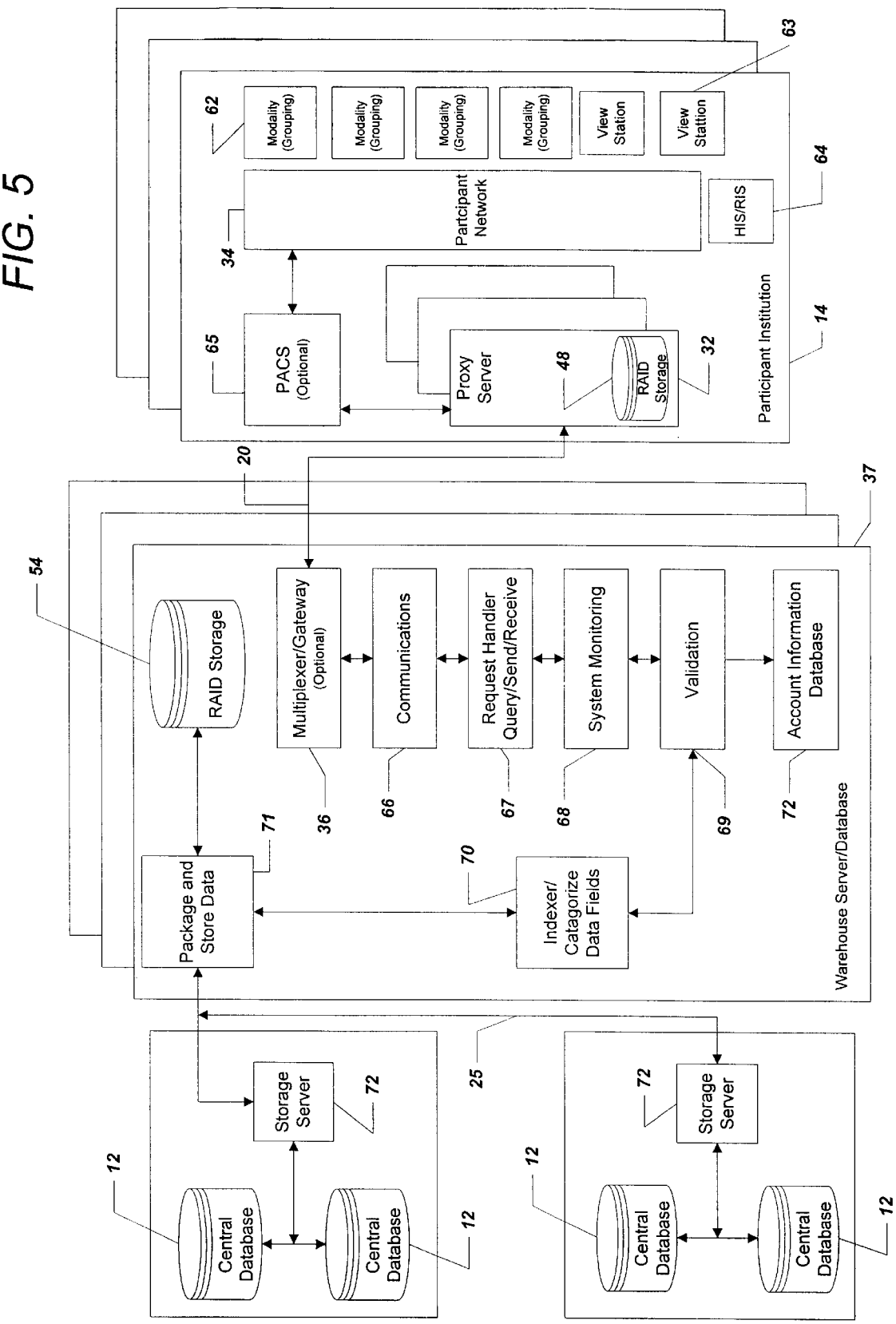
FIG. 5 is a block diagram of a portion of the database and communications device and method of FIG. 1 and FIG. 2 detailing the data delivery and communication system between the institutional clients and the system devises.

Referring to FIGS. 1, 2 and 5, the construction, maintenance and operation of central database 12 is described. Central database 12 is one or more host rack mounted computer servers or warehouse servers 37 preferably having system requirements of one 42U Rack or equivalent, with Linux version 6.2 or newer operating system, one or more HP LH4r servers or equivalent, at least one 500 Mhz XEON processor or greater, 4 GB of random access memory, Keyboard, Mouse, two or more 300 GB, more or less, RAID-5 disk array, a VGA color monitor, an APC 2200 rack mount UPS, one or more Pioneer DRM-7000, or equivalent, jukeboxes, one or more DVD writers 38, one or more DVD readers 39, and a standard Intel PC workstation with a Linux operating system 40 configuration. The host operates a message router for handling messages, notices and alerts between the central database 12 which also acts a redundant database, and participant institutions 14, an institutional account database as discussed in more detail with reference to FIG. 5; one or more gateway devices 36 comprising software for routing network traffic.

Referring to FIG. 2, the device and method 10 of digital data and image storage, retrieval, and delivery communications links is described beginning with participant network 34. Participants' network 34 input delivery transactions to the proxy server 32 for delivery to the central database warehouse server 37 through an Internet/VPN 35 communication link. Delivery instructions, as described below with reference to FIG. 7, and accompanying data are stored in the proxy server 32 and the warehouse server 37, and then transferred to the central database 12. The central database 12 is an array of optical disks or other storage devices configured to operate as a long-term permanent storage archive. Once the data attached to the delivery instructions is received by the warehouse server 37, it is temporarily stored to RAID storage and permanently stored or written to DVD or its equivalent by the DVD writer 38 or stored on equivalent storage media. The instructions include information such as query requests, storage requests, retrieval requests, DICOM header and study grouping information, and other participant institution 14 or patient identifiers or information, including account information. In this regard, the type of information stored on the database 12 is much more detailed and thorough than that anticipated by current technological standards.

The communication link is transmitted over any TCP/IP connection. TCP/IP is a common protocol that can be used over almost any communications medium including the Internet. All communications to and from the proxy server 32 by the warehouse server 37 are secured transmissions using a combination of three specifically design features: (1) all communications will be transmitted to and from known Internet Protocol (IP) addresses; (2) a proprietary protocol will be used for all communications to and from the institutional participants' site and the warehouse server 37; and (3) all communications will be digitally encrypted. These communication protocols will utilize the proxy server 32 and/or the warehouse server 37 as the mechanism for establishing, maintaining, monitoring, and terminating the communication link. In addition to simple communications, the links between the warehouse server 37 and the institutional participants will provide for a continuous flow of management information (such as transaction processed/queue/status/etc.) between the participant and the host. Monitoring, upgrades and reconfigurations of the participant proxy server 32 can be made remotely via the communications link.

Each set of delivery instructions and accompanying data on database 12 is stored and retrievable under a unique identifier or identifiers. The identifiers comprise an identification of the particular instruction set for the named participant institution. For example, the participant institution are likely to have numerous delivery instruction sets depending on the type of image, type of modality, attending doctor, patient name and address, department, and patient identifier number, but also based on the date and time the image was produced, which doctor ordered the procedure, and billing criteria. The identifier may also include an institution acronym.

Figure 7:
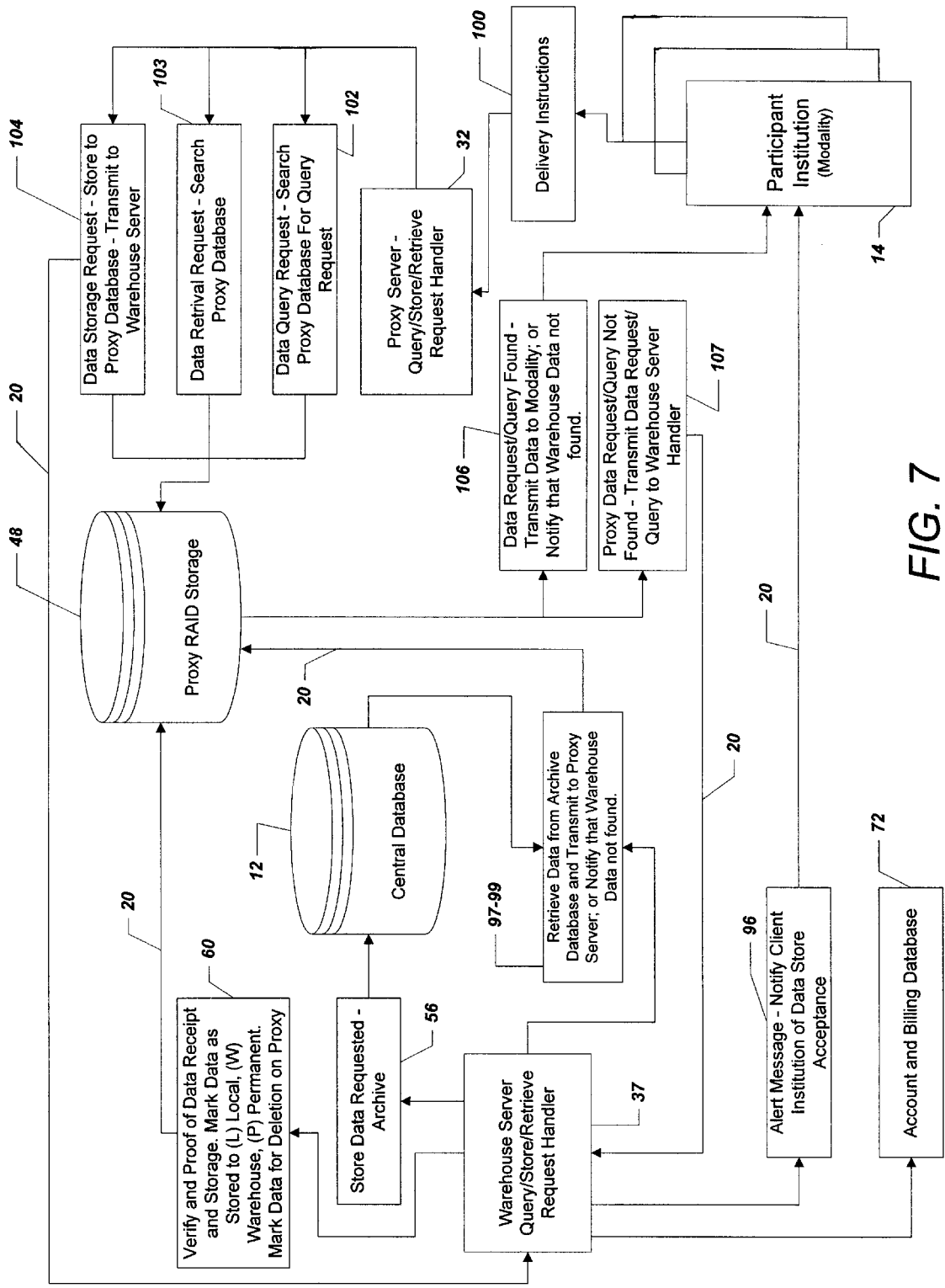
FIG. 7 is a block diagram of a portion of the database and communication device and method of FIG. 1, FIG. 2 and FIG. 5 detailing various data query, storage, and retrieval transmissions between the institutional clients and the system devices.

As the delivery instructions are received, verified, validated, categorized, packaged and stored to the central database 12, alert messages as described below with reference to FIG. 7, are generated by the warehouse server 37 for communication along links as described below with reference to FIG. 7, to the participant institution informing them of the delivery of the instruction set and storage of the data or image. In this regard, it is understood that the central database warehouse server 37, the proxy server 32, and the participant network 34 include a wire or wireless transceiver for receiving data for storage and query and retrieval requests, and for transmitting alerts and received data and information.

Figure 3:
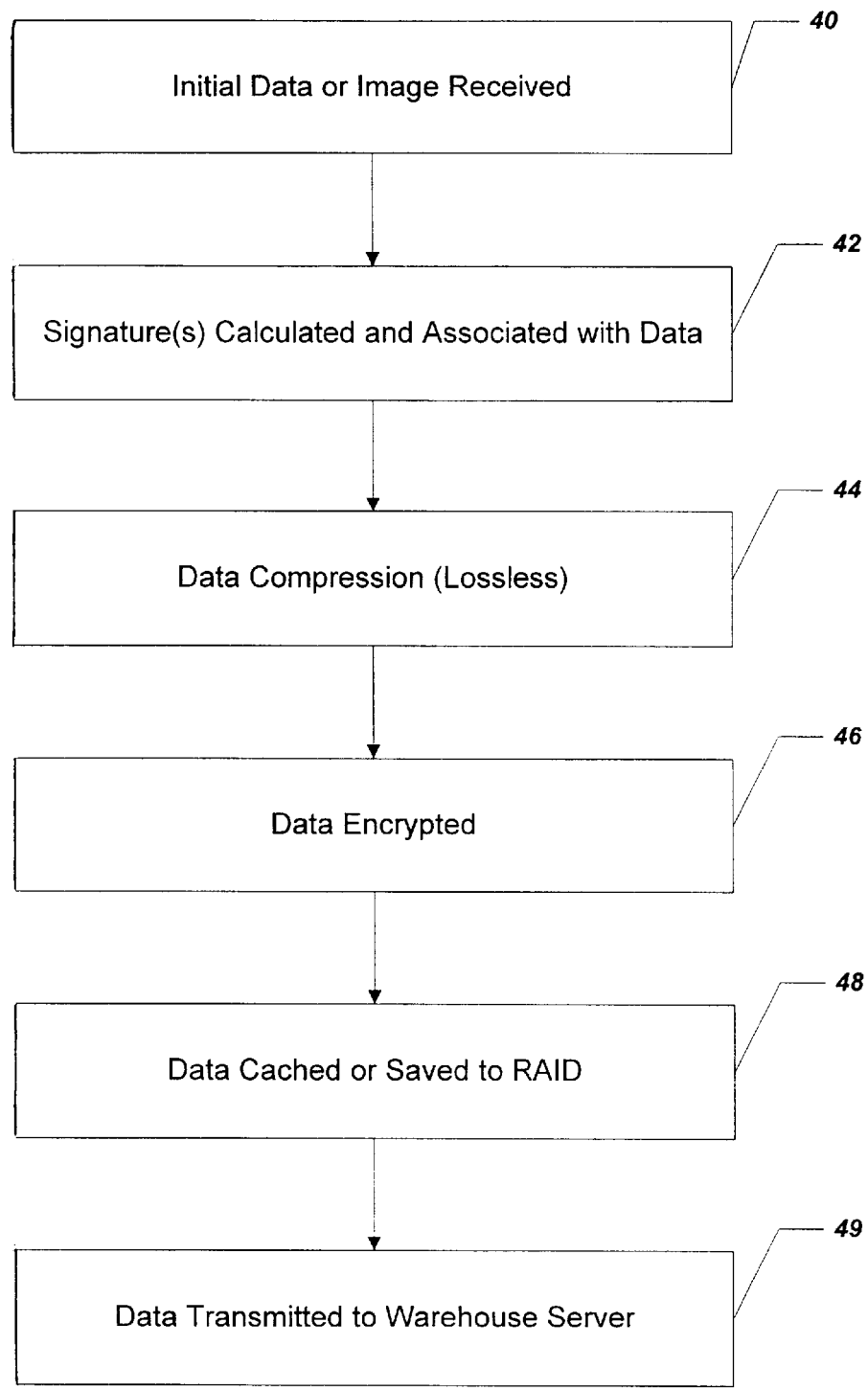
FIG. 3 is a block diagram of a portion of the database and communications device and method of FIG. 1 and FIG. 2 for processing data transmitted form institutional clients to a system device.

Referring to FIG. 3, the proxy server upon acceptance of delivery instructions automatically calculates the particular instruction sets as initial data received 40. Upon calculation that the requested transaction is a storage request the proxy server calculates and associates a digital signature 42 with the received data or image. The digital signature is a compact representation of all data within the transaction. By comparing an existing transaction signature with a newly calculated signature, any data changes can be detected. The digital signature is used to ensure data and/or image integrity in memory, on disk, during transmission, and through long-term storage and eventual retrieval.

The data or image is then automatically compressed 44, unless such data and images are unable to be compressed, is already compressed, or compression or re-compression is not optimal. The compression facilitates the communication and transmission of the transaction between the participant institution and the warehouse server and central database. A "lossless" compression mechanism is utilized to perform the compression task. By "lossless" it is meant that the process performs data or image compression without performing any irreversible data compression or loss of data. Compression is utilized to facilitate or increase data or image transmissions between the proxy server and the warehouse server, and well as to decrease the amount of disk space utilized for storage. Lossless compression will allow the original transaction (bit-for-bit) to be reconstructed from the compressed representation after transmission. Transactions received by the proxy server from the warehouse server are "losslessly" de-compressed, where appropriate, before being transmitted to the participant's network and modalities.

After compression the proxy server automatically encrypts the data or image 46 prior to saving it to the RAID 48, and transmission of the data or image to the warehouse server 49. The system device and method 10 utilizes a minimum 128-bit encryption algorithm. Once the initial data or image received 40 is digitally signed, compressed and encrypted the proxy server automatically saves the data or image to its RAID storage, and then transmits the data or image to the warehouse server 49 located at the central database over communications links 20 as shown in FIG. 1.

Figure 4:
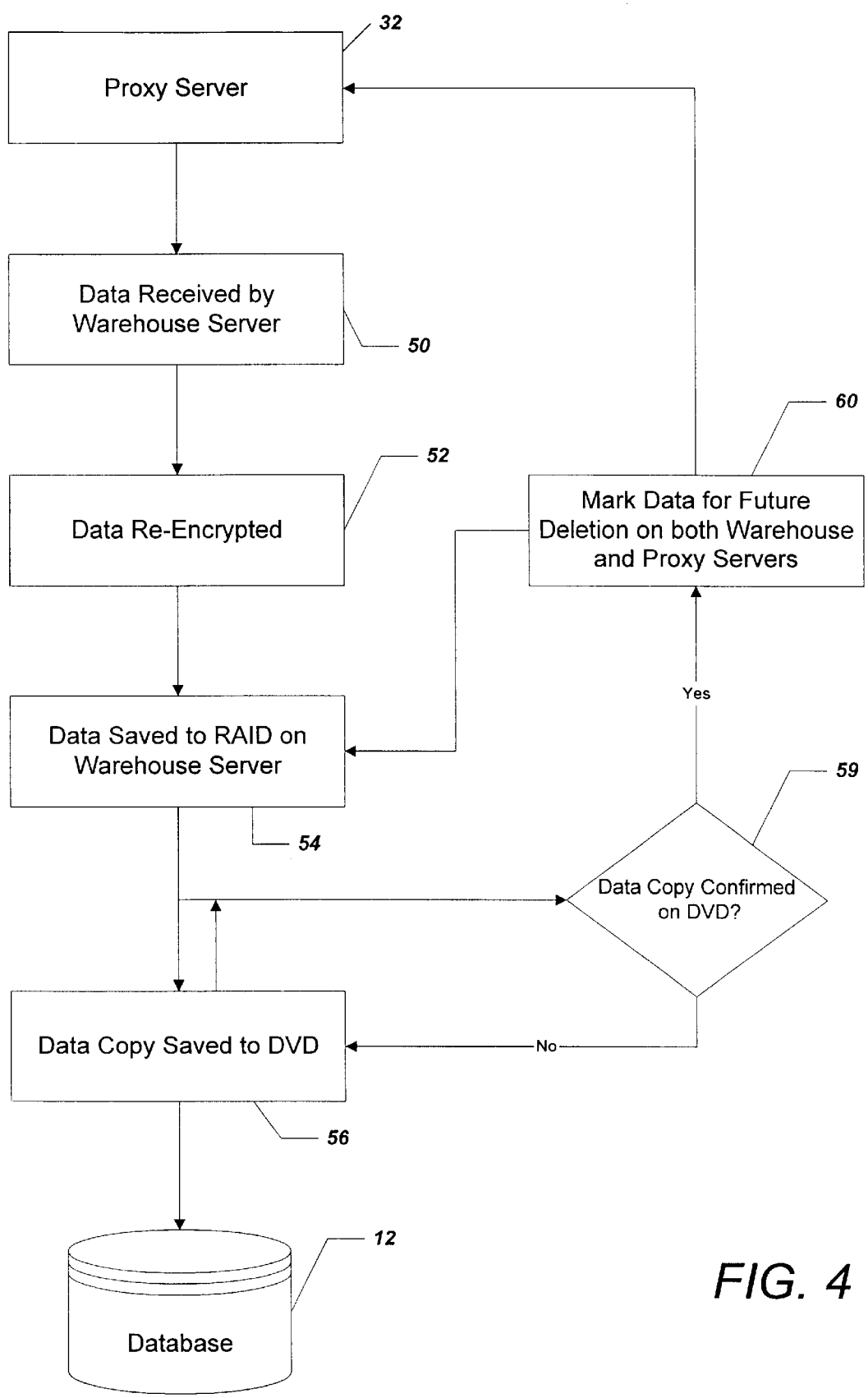
FIG. 4 is a block diagram of a portion of the database and communications device and method of FIG. 1 and FIG. 2 for processing data transmitted form institutional clients to a system device.

The proxy server acts as both a storage or cache device and a communications device connected along communications links to the warehouse server located at the central database. Referring to FIG. 4, after the data or image is transmitted by the proxy server 32 and received by the warehouse server 50 the data or image is possibly re-encrypted 52, and then automatically stored or saved to the warehouse server's RAID storage 54. Once the data or image is saved to the RAID storage, a copy of the data or image is saved to an optical DVD or its equivalent disk 56, or equivalent, and then placed in the database 12. The database is comprised of one or more DVD jukeboxes, or equivalent optical disk, or tape-drive, RAID or other storage devices. The warehouse server automatically runs a calculation to confirm 59 that the data or image has been properly copied to DVD disk, or equivalent, in the database. If the copy is confirmed, then the warehouse server automatically marks the original data or image electronically as deleteable 60, at a future date, on both the warehouse server and the proxy server. Subsequent to deletion the only remaining copies of the data or image will be located at the central database and the redundant database. Referring again briefly to FIG. 1, the central database 12 can be comprised of one or more databases located remotely from each other, each acting as a redundant back-up database for the other for purposes of storing data and images for retrieval in case of disaster or destruction of the other database. Once the data or image is permanently stored to the central database 12, a minimum of two copies of such data or image are always maintained at the database for the storage life of the data or image.

The type of data and images transmitted over the communication links 20 preferably complies with DICOM standards, although the device and method 10 can accept and process requests for query, storage, retrieval, and delivery of data and images that do not comply with this standard. FIG. 5 is a block diagram detailing the delivery of data and images transmitted along communications links 20 of the device and method 10, in accordance with the invention. The device and method 10 preferably comprises a duel server system configuration providing communications between the central database 12 and the participant institution 14 along communications links 20, thereby providing a secure communication system for the transmittal of digital data and images from the participant institution 14 to the central database 12. By "duel server" is meant one or more servers, either linked or not linked together, located at the central database 12 comprising minimum system configuration requirements as described above for the warehouse server 37, and one or more servers, either linked or not linked together, located at the participant institution 14 comprising minimum system configurations requirements as described for the proxy server 32 above. This system design allows for independent servers located at both the central database 12 and the participant institution 14, providing for the ability of both of these server systems to work independently during any temporary communications link 20 failure.

The invention preferably provides a participant institution 14 proxy server 32 to warehouse server 37 system the purpose of which is to directly connect to and interface with the participant institution's 14 network 34, radiology modalities 62, view stations 63, Hospital Information System/Radiology Information System (HIS/RIS) 64, and PACS 65 to strategically store or cache DICOM or non-DICOM data or image transactions from the participant institution 14 utilizing the proxy server 32, and then efficiently transmit that data and images to and from the warehouse server 37 and the central database 12 for the purpose of creating a long-term digital archive of the data and images in the central database 12 that is continuously and uninterruptedly accessible to the participant institution 14 during the term of the storage life of the data or image. The transmittal of data and images between the proxy server 32 and the warehouse server 37 is over wire or wireless communication links 20–23 which communication links are most preferably either, or a combination of, the Internet, Virtual Private Network (VPN), and dedicated lines.

Preferably the proxy server 32 is located at the participant institution's 14 physical site location and is connected directly into the participant network 34 either through or not through the participant institution's PACS 65. Once connected to the participant network 34 the proxy server 32 has direct access, connectivity and communication with the participant institution's radiology modalities 62, view stations 63, and HIR/RIS 64, and can be in a communication mode with any authorized network device existing on the participant network 34, such as PCs, workstations, and dumb terminals. The proxy server 32 layer preferably interfaces with DICOM compliant medical radiology modalities 62 located on the participant's network 34, for the purpose of either manually or automatically providing a communication and storage device for transmitting and storing various DICOM or non-DICOM compliant data and images generated from such modalities. The proxy server 32 layer includes and encompasses all necessary DICOM specific communication protocols, and has the ability to send, receive and request specific transactions to and from the various modalities 62, and the warehouse server 37 and central database 12.

The proxy server 32, in accordance with the device and method 10, preferably acts as both a communication device and a storage device. As a communication device the proxy server 32 transmits queries, requests, and data and images received from or sent to participant network 34, modalities 62, view stations 63, HIS/RIS 64, PACS 65, and other authorized network devices to and from the warehouse server 37 and the central database 12 over communication links 20. The proxy server 32 preferably also acts as a DICOM server layer interfaces with participant institution 14 DICOM compliant medical equipment or radiology modalities 62. This layer encompasses all necessary DICOM specific communications protocols, and has the ability to send and request specific transactions to and from the proxy server layer. The proxy server 32 DICOM layer functionality preferably includes, but is not limited to, DIMSE services; STORE—save a DICOM transaction (image); GET—retrieve a previously stored DICOM transaction (image); FIND—find a transaction or set of transactions based upon meta data criteria; MOVE—move a transaction from the DICOM server to another DICOM compliant device; the software has ability to act as a DICOM protocol user or DICOM protocol provider. The device and method 10 also incorporates an HIS/RIS interface software layer.

Operating in this capacity the proxy server also preferably acts as a temporary cache or RAID storage 48 for data and images transferred for or from the participant institution 14. Data or images transmitted from the participant network 34 modalities 62 are stored on the proxy server for varying lengths of time based on the particular participant institution's 14 requirements. Typically, this storage time period runs from one day to sixty days and can run as long as three hundred and sixty days or longer depending on the participant institution 14. The proxy server 32 configuration is adaptable to accommodate varying RAID storage 48 requirements. Subsequent to deletion of the data and images temporarily cached on the proxy server 32 RAID storage 48 the data and images is re-stored on the proxy server 32 by the warehouse server 37 when a participant institution 14 requests data and images from the central database 12, as described below with reference to FIGS. 6 and 7.

The warehouse server 37 is connected directly to the proxy server 32 over communication links 20 and acts as a communication 66 device, a request handler 67, a system monitor 68, a transaction validation 69 device, and a temporary RAID storage 54 device. Data and images are transmitted over any TCP/IP connection from known Internet Protocol (IP) addresses using a proprietary protocol both to and from either the proxy server 32 or the warehouse server 37. Preferably the warehouse and proxy server system is comprised of two or more servers operating both independently and in conjunction with each other. All transmitted communications are also preferably encrypted in accordance with the standard as described above. Once a transmitted query, storage or retrieval request is received by the warehouse server's 37 request handler 67 it is automatically validated and processed. A query or retrieval request will automatically generate a search of the warehouse server's 37 RAID storage 54 and central database 12 for the requested data or image, and transmit the requested data or image or information back to the proxy server for transmittal to the participant institution's network 34, modalities 62, view stations 63 as directed by the participant institution's PACS 65, HIS/RIS 64, or other system configurations or delivery instructions 100. A storage request will automatically be processed through the indexer/categorize data fields 70 and be packaged and stored 71 to both the RAID storage 54 and central database 12 DVD jukebox or equivalent storage device. Storage request data and images in addition to being stored on the central database 12 located at the receiving warehouse server are also preferably transmitted over communication link 25 to a redundant central database 12 for storage and archival. Preferably each central database 12 is controlled and operated by its own storage server 72, which operates as both a storage and communication device similar to the warehouse server. Storage servers are an optional device of the device and method 10 in accordance with the invention.

The warehouse server also preferably performs gateway or security functions by regulating the types of transactions allowed to be processed. Unauthorized transactions or communications transmitted from unknown users are blocked by the multiplexer/gateway 36, or software equivalents, thereby preventing unauthorized access to the central database 12. The warehouse server 37 automatically monitors 68 the system components and stored data and images on the system on a periodic basis to insure and verify data and system component integrity. In this respect data elements and digital signatures are compared periodically to prove data integrity and authentication. Periodic reporting on the monitoring results are automatically transmitted, collected and stored on the system for historical reference.

The warehouse server also preferably compiles and transmits accounting information on the data and images stored to the system for billing purposes. This information is automatically transmitted to the account information database 72 for account reconciliation and participant institution 14 invoicing purposes. Monthly invoices detailing the number of studies stored to the device and method 10 are complied form this information and transmitted to the participant institution for payment.

Figure 6:
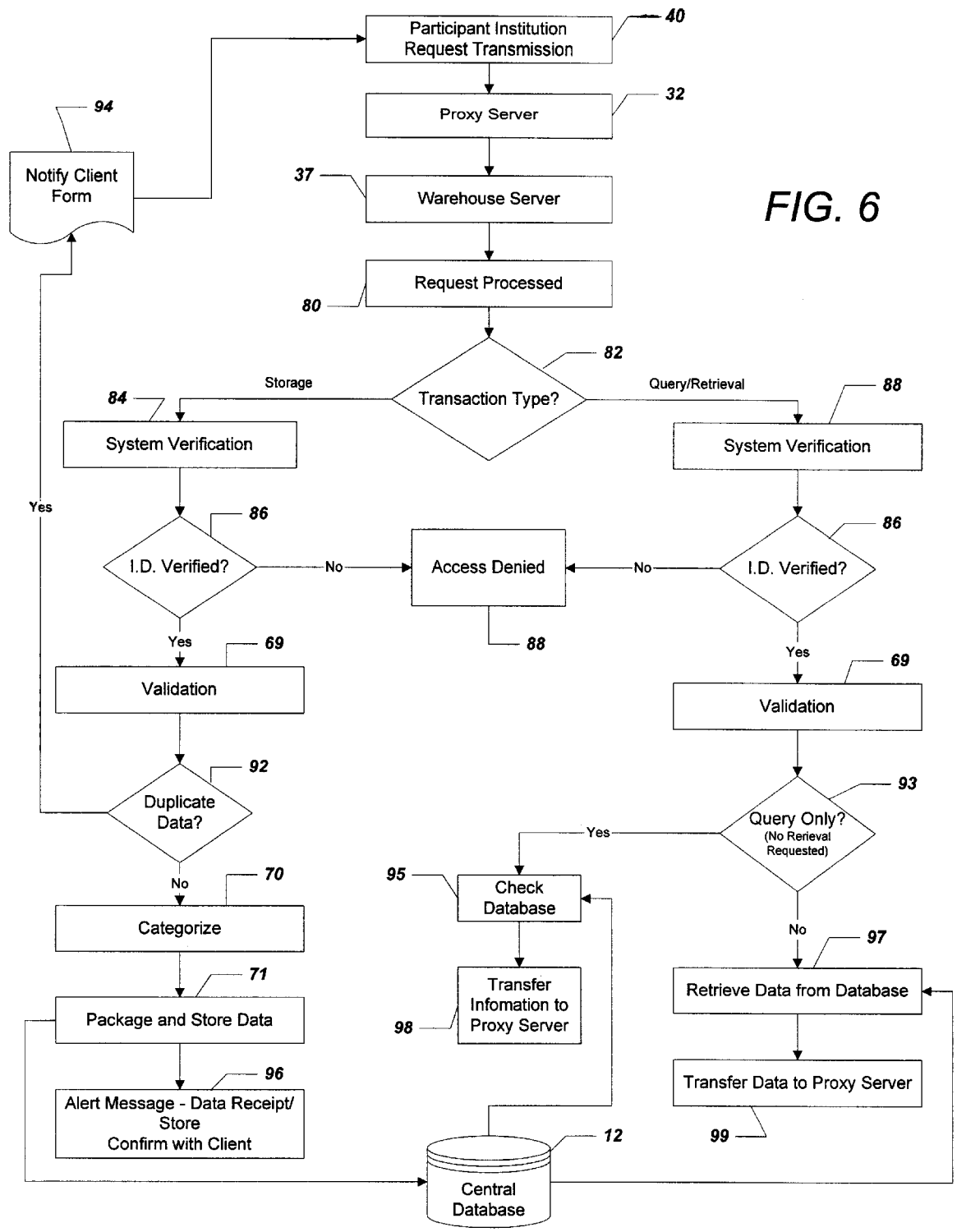
FIG. 6 is a block diagram of a portion of the database and communication device and method of FIG. 1, FIG. 2 and FIG. 5 detailing various data query, storage and retrieval request transmissions from institutional clients to the system devices.

Referring to FIGS. 6 and 7, the device and method 10, in accordance with the invention, provides query, storage and retrieval functions thereby providing participant institutions 14 and their institution satellite locations 18 with the ability to transmit and communicate request to the device and method 10 preferably for the purpose of electronically querying to the system with instruction sets for information, and making data and/or image storage or retrieval requests for either the storage of data and images to the central database 12 or the retrieval of data and images from the central database 12. In this respect data and images requested for retrieval and queries for information are simultaneously made to the proxy server 32, the warehouse server 37, and the central database 12, with return responses being delivered from either the proxy server 32, without communication to the warehouse server 37, or the warehouse server 37 depending on the storage location of the data and images or query information sought or requested. The proxy server 32 and the warehouse server 37 preferably act both independently and together for the purpose of locating and returning a response to the participant institution 14 or institution satellite location 18 depending on the request generated.

Referring briefly to FIG. 7 the proxy server 32 request handler processes the specific request and automatically directs it according to type. Request types are preferably data query 102, data request retrieve 103, and data request storage 104. Once a request is received and directed according to type the proxy server automatically processes the request based on its instruction sets. For example, a storage request will automatically direct and save the data and images to the proxy server's RAID storage 48 and then automatically transmit the request and data and image over communication link 20 to the warehouse server 37 to be saved in accordance with the storage rules as set by the system software. A data query will automatically direct a query search of the proxy server RAID storage 48 for the specific query information, and if the information is found it is automatically transferred 106 to the participant institution 14 in accordance with the specified instruction set. If the query request information is not found on the proxy server RAID storage 48 the request is automatically transmitted 107 to the warehouse server 37 where the request is processed in accordance with the query/retrieval steps detailed in FIG. 6. Once the query is processed, the requested information is transmitted 98 to the proxy server 32 over communication link 20 and re-stored on the RAID storage 48 where the information is then automatically transmitted 107 to the participant institution 14. If the warehouse server fails to find the query request information on either its RAID storage 54 or the central database 12 a notice is transmitted back to the proxy server in the same manner for transmittal to the participant institution 14. Likewise, a request for data retrieval 103 is processed in the same manner as a data query request 102, with the data and images being transmitted 99 to the proxy server 32 over communication link 20.

Figure 9:
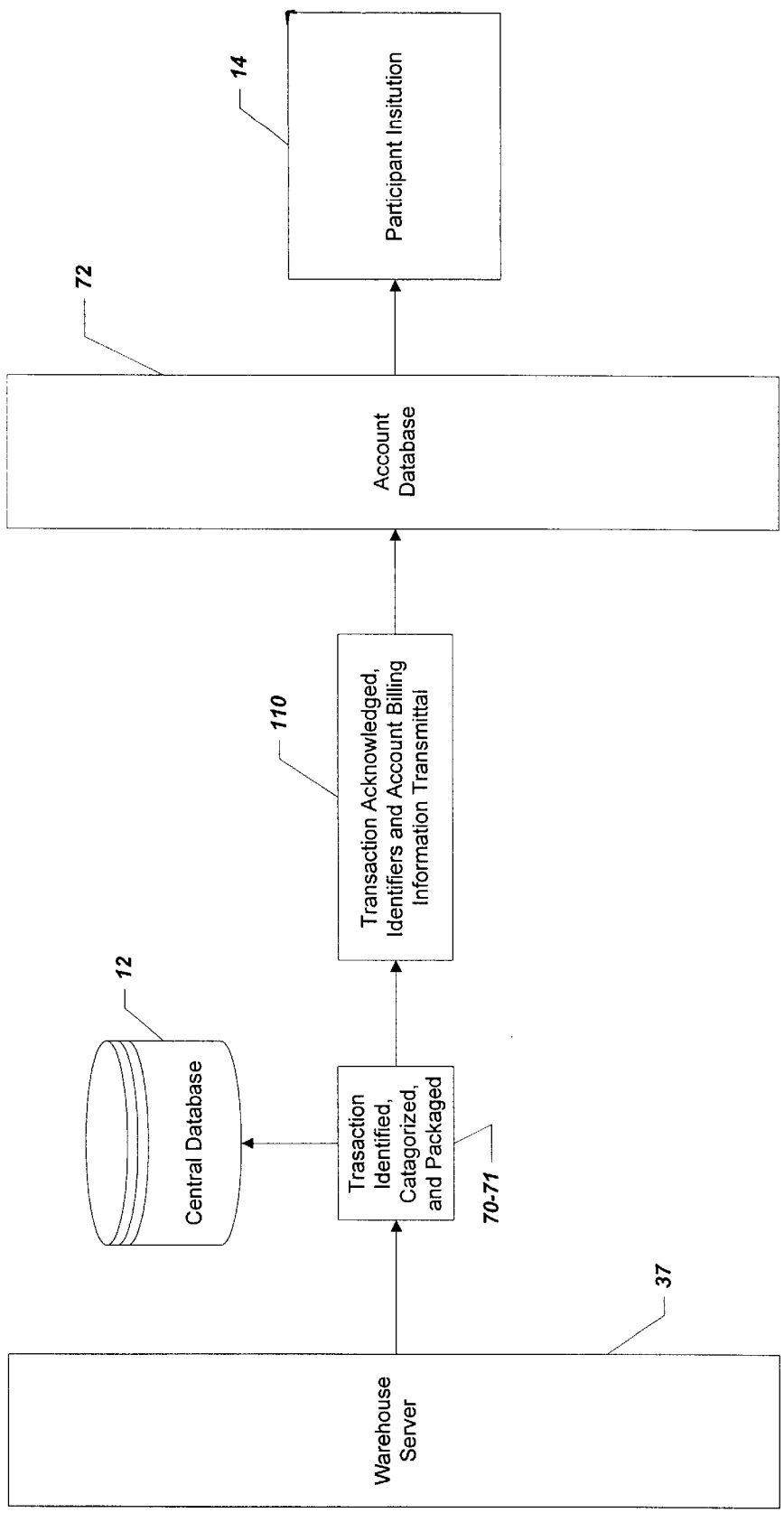
FIG. 9 is a block diagram of a portion of the database and communication device and method of FIG. 1, FIG. 2 and FIG. 5 detailing the transmission of account data received from institutional clients between system devices.

Referring again to FIG. 6, once a query, storage or retrieval request is received and transmitted to the warehouse server 37, it is processed 80 and the system software calculates a decision as to transaction type 82 and directs the request based on a decision of whether the request is for storage, retrieval or a query for information. Delivery instructions are automatically carried out depending on the type of request received. A request for storage generates a system verification 84 response from the software and the request sender's identification is verified 86 by the system. Once the sender's identification is verified the system automatically conducts a transaction validation 69 to determine if the transactions is an acceptable or non-acceptable transaction type. An unacceptable transaction is terminated. An acceptable transaction is then tested against the database to determine if the storage request is a duplicate 92. If the storage request is a duplicate or partial duplicate of already existing data to device and method 10 will selectively save one or the other storage request, save both storage requests, or based on criteria specific software ask an external device or person at the participant institution 14 to make a decision as to which storage request to save. Additionally, a notice form 94 is generated and sent to the sender notifying it that a request to store duplicate data and images has been received. Once the storage request is accepted the data and images are categorized 70 (indexed), packaged and stored 71 to both RAID storage in the warehouse server 37 and optical DVD disk or equivalent on the central database 12. A notice is then generated automatically by the warehouse server 37 notifying the sender that the data and images have been successfully stored to the central database 12. A request for query or retrieval data and images is handled in the same manner as a request for storage. After validation the system software automatically calculates whether the request is for a query only 93 or a request for retrieval of data and images. For example, a query only request type can be a request for verification of the storage or archival of specified data and images without a request to retrieve the data and images. Upon verification that the request is for query only, the system software, in accordance with the instruction sets, checks the central database 12 for the requested information and transmits 98 a response back to the proxy server 32 where the information is either re-stored to the proxy server RAID storage 48, or forwarded to the requesting device or person. A request for retrieval of data and images will generate a system response as detailed above. Referring to FIGS. 6, 7 and 9 a data storage request will automatically generate transaction acknowledgement, identifiers and account information for transmittal and storage 110 on the system's account information database 72. Account information stored on the account information database 72 may be retrieved from the database using unique account identifiers for each set of account information. The account identifiers, as with data and image identifiers, comprise an identification of a particular account at the named participant institution 14, and may also include specific patient identifiers and institution's name or acronym. Account information is periodically transmitted to participant institutions for invoice billing purposes, either electronically over communication links 20 or in hardcopy via U.S. mail or private carrier.

Figure 8:
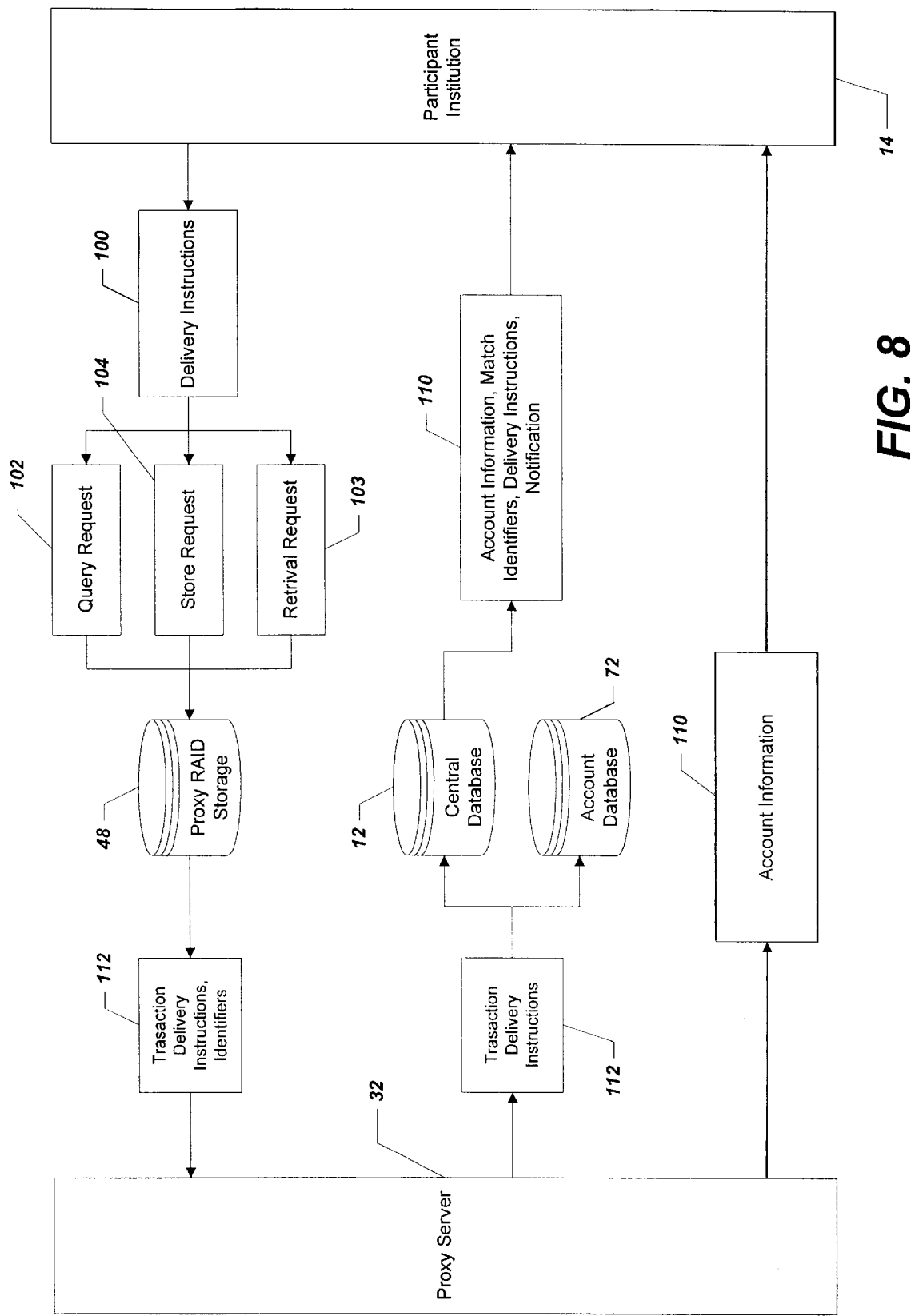
FIG. 8 is a block diagram of a portion of the database and communication device and method of FIG. 1, FIG. 2 and FIG. 5 detailing the transmission of various data query, storage, and retrieval request between the institutional clients and a system device.

Referring to FIG. 8 the device and method 10 preferably operates as a communication and storage device at the speed of the participant institutions 14 computer network 34. Typically, DICOM communications range from 10 to 100 Mbps (Mega bits per second) per device. The typical high-speed communication links 20 between the participant institution 14 and the central database 12 operate at 1.5 to 45 Mbps. This imbalance creates the need for transactions to be cached or stored at the participant institution's 14 site in a manner that creates a direct link to the participant's network 34. The more cache, the better the digital image retrieval performance. The device and method 10, in accordance with the invention, preferably is connected directly to the participant network 34 by the proxy server 32, and operates as a communication and storage device at the speed of the participant network 34. This provides a high-speed communication and storage link to the participant network for the purpose of processing query 102, storage 104 and retrieval 103 request transactions in accordance with the delivery instructions 100. The proxy server 32 software is designed to cache or store transactions temporarily in accordance with the system specifications. This provides the participant institution 14 with an on-line or immediate archive of its data and images for a specified period of time. The specific software algorithms are designed to cache or temporarily store the "most likely" used/retrieved DICOM or non-DICOM transactions (data and images) on the proxy server RAID storage 48. Once the data and images are cached they will be held for a specified period of time based on predetermined storage algorithms. As these data and images are received and cached from the participant's modalities 62 the data and images are automatically compressed, encrypted and transmitted along communication links 20 to the warehouse server 37 for long-term archival on the central database 12. After these data and images are transmitted and stored on the central database 12, they are tagged as expendable within the proxy server cache or RAID storage 48. Preferably deletion of the "expendable" data and images from the proxy server 32 will occur between 30 and 60 days from the initial cache date depending on the participant institution's 14 requirement, but the data and images can be cached on the proxy server 32 for extended periods of time up to and/or exceeding twelve or more months. Once the data and images are deleted from the proxy server 32 any request for that particular data or image must be retrieved from central database 12. These requests will all be channeled automatically through the proxy server 32. Because data or image retrieval from the central database 12 over communication links 20 can be a slow process (depending on the participant institution's server connection speed), when a image is retrieved, it is also re-cached within the proxy server 32 for an additional period of time based on the particular participant institution's 14 requirements.

Figure 10:
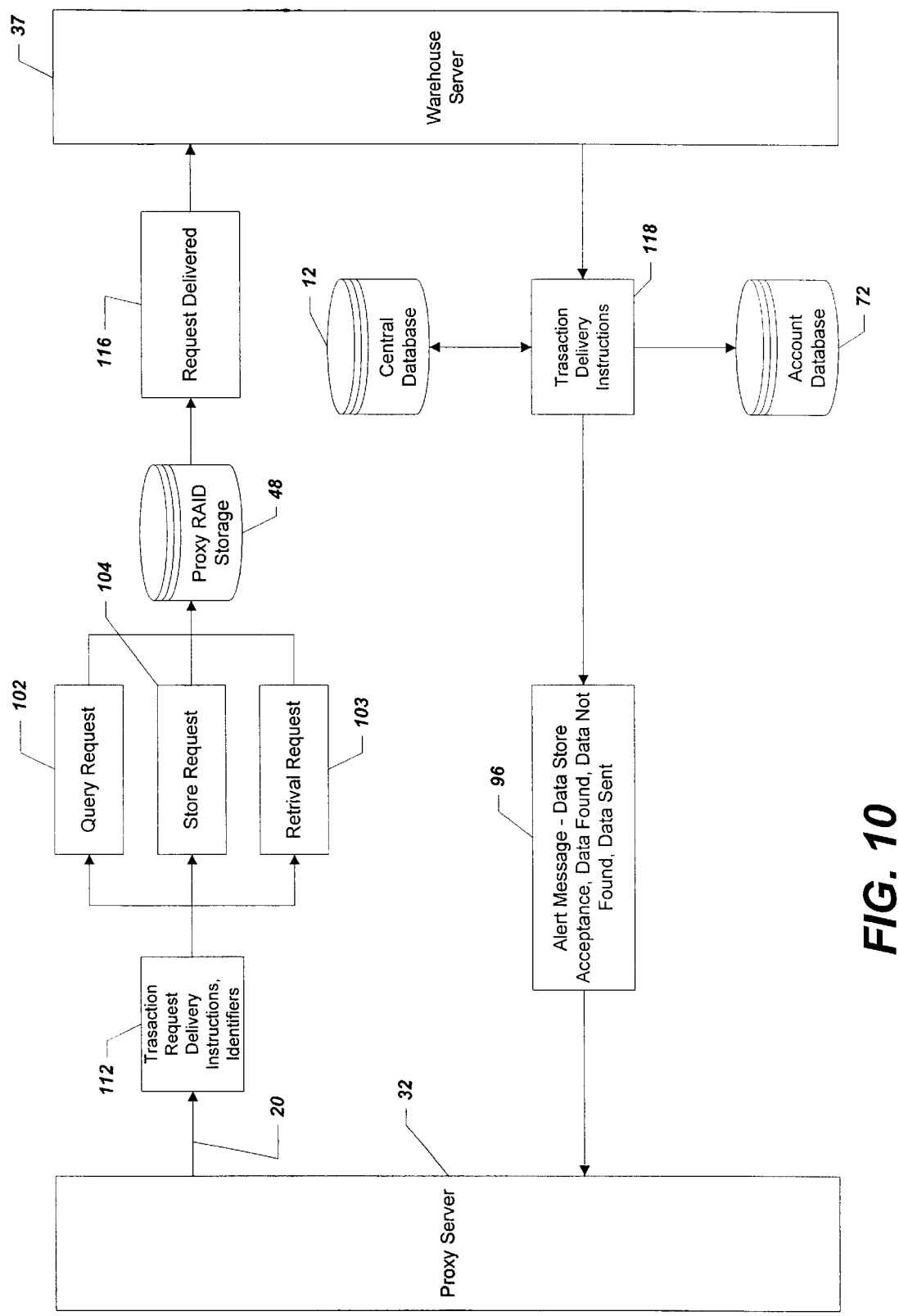
FIG. 10 is a block diagram of a portion of the database and communication device and method of FIG. 1, FIG. 2 and FIG. 5 detailing the communication of query, storage, and retrieval request data received from institutional clients between system devices.

Referring to FIG. 10, additional mechanisms are provided within the device and method 10 to allow data and images to be pre-cached to the proxy server 32 from the warehouse server 37 and central database 12 in anticipation of near future use by the participant institution. Other basic tasks of the warehouse server 37 are to monitor of all transactions and operations related to the system as a whole to ensure that participant institution 14 systems and the proxy server 32 are functioning properly, that the communications links 20 are transmitting correctly, and that the participant institution's 14 systems are accurately configured and up to date. In this regard, the warehouse server 37 preferably will periodically check the integrity of all managed transactions by comparing the stored transaction with a derived digital signature. Any changes to the data caused from either media degradation or deliberate tampering will be detected during the integrity check. The warehouse server 37 software innately understands the database aspects of DICOM transactions. As such, all relevant meta information is automatically copied from incoming transactions and stored in an index or central database 12. This database allows the meta fields to be searched and either retrieved locally from the proxy server 32, or by the participant institution 14 from the warehouse server 37 or database 12 through the proxy server 32 over communication links 20. Additionally, the central database 12 contains one or more live links or reference to the complete DICOM transaction stored in either the proxy server 32 or warehouse server 37.

Figure 11:
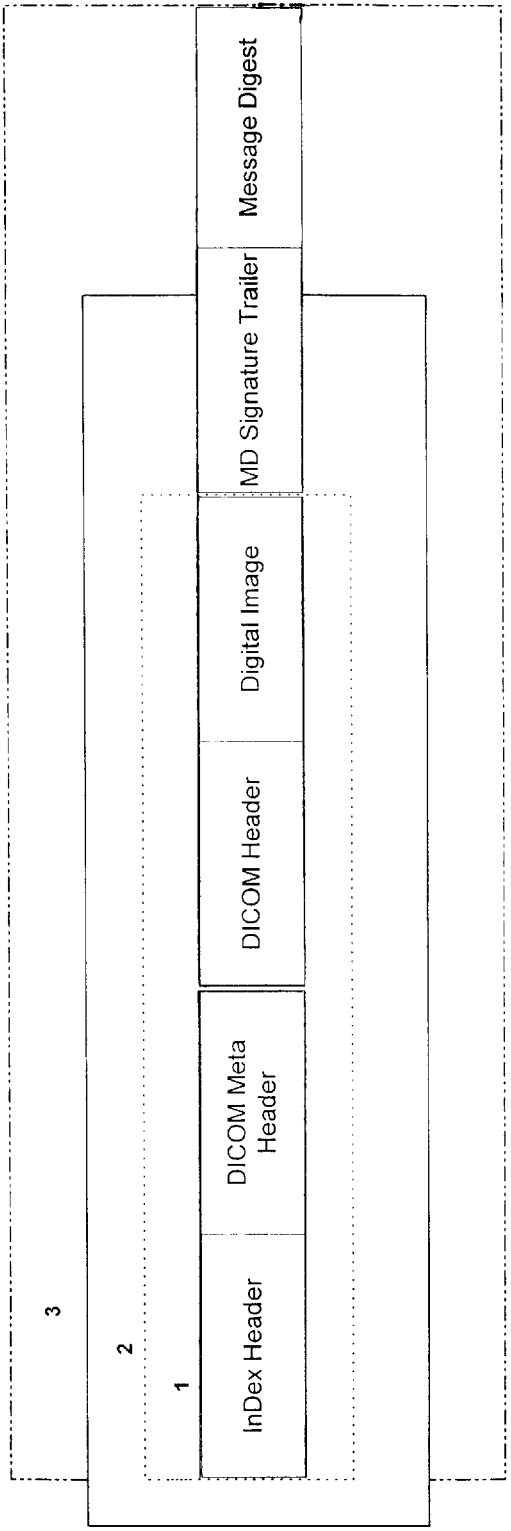
FIG. 11 is a block diagram of a portion of the database and communication device and method of FIG. 1 detailing the application of digital signatures to data transmitted and received from institutional clients.

FIG. 11 generally illustrates transaction within the described system. The transaction can be formed by first calculating a digital signature of the original digital mage and storing it within the Index header. Optionally, the digital image can be replaced by its compressed representation. Optionally, DICOM Meta Header and DICOM Header, each can be signed by a respective digital signature, which is stored within the index header.

The grouping of Index Header, DICOM Header and DICOM Meta Header, and digital image are digitally signed with a pendant digital signature or trailer.

This combined package can optionally be encrypted, and this newly encrypted message can be digitally signed and appended with another digital signature, referred to as a message digest.

For example, an X-ray of Mr. Doe is moved from a participated institution to the institution server. In this case, the original image would have a digital signature calculated and stored in the index header of the institution server. This stored image will be optionally compressed. Also optionally, DICOM Header, which is a non-image part of the transaction, and DICOM Meta Header, which contains additional information, can be digitally signed and/or compressed so as to have their digital signatures stored in the index Header.

This combined transaction including Index, DICOM META and Dicom Headers along with the digital image is digitally signed and appended to the transaction. This newly created transaction can optionally be encrypted and then digitally signed and appended with yet another digital signature or message digest. The above-described procedure provides a mechanism of compactly, accurately, securely representing the original information.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for communication, storage, retrieval and delivery of information comprising:
    an institution server having random access memory (RAM);
    an institution database accessible by said institution server;
    software executing on said institution server for receiving information selected from the group consisting of header, images and data associated with header and each of the images from a healthcare institution;

software executing on said institution server for storing the received images on said database;

software executing on said institution server for generating an index based upon the received information, and for storing the index in a storage selected from the group consisting of the RAM, institution database and a combination thereof;

a central server;

a central database accessible by said central server;

a communication link between said central and institution servers;

software executing on said central server for receiving the information from said institution server through the communication link;

software executing on the central server for storing the information on said central database;

software executing on said institution server for automatically searching the index in response to a query, and for searching the warehouse server if the information has not been found on the institution server or the institution database;

software executing on said warehouse server for transmitting the information to the institution server for storage thereon in response to the query; and software executing on said institution server for temporarily storing on the institution server and institution database, based upon various selected criteria, the retrieved information in anticipation of near future use by the institution.

2. The system defined in claim 1 further comprising an institution network interconnecting electronic devices selected from the group consisting of at least one Hospital information System (HIS) terminal, at least one Radiology Information System (RIS) terminal, at least one computer, at least one viewstation, at least one MRI machine, at least one X-ray machine and a combination thereof, a communication link between the institution network and the institution server, and software executing on the institution network for transmitting images and data to the institution server via the communication link.

3. The system defined in claim 2 wherein institution network further includes software for receiving the information from the institution server.

4. The system defined in claim 2 wherein the transmitted data includes at least one set of delivery instructions, which includes information selected from the group consisting of query requests, storage requests, and retrieval requests and a combination thereof, a DICOM header, study group information, institution identifiers and patient identifiers.

5. The system defined in claim 4 further comprising software executing on the institution network for generating an account identifier which is associated with a sender generating each of the query, storage and retrieval requests.

6. The system defined in claim 3 wherein the index is based on the institution and hospital identifiers selected from the group consisting of a type of image, type of modality, attending doctor, patient's name, birth date, sex, and physical characteristics, diagnosis, the date and time the data and image were produced and last accessed, account number and a combination thereof.

7. The system defined in claim 2 further comprising software executing on the institution server for authorizing transmitting of the information, and software for verifying integrity of the authorized information and including a digital signature which is selectively used to ensure the integrity of the information stored in the institution server.

8. The system defined in claim 7 further comprising software executing on each of the institution and central servers for calculating the digital signature representing at least one piece of information of the transaction, and software executing on each of the institution and central servers for comparing the calculated digital signature with an existing signature to detect any changes in the information.

9. The system defined in claim 2 further comprising software executing on the institution server for selectively losslessly compressing the information received from the institution network.

10. The system defined in claim 9 further comprising software executing on the institution server for encrypting the compressed information.

11. The system defined in claim 10 further comprising software executing on the institution server for temporarily storing the compressed and encrypted images on the institution database, wherein the institution database is selected from the group consisting of a Redundant Array Of Independent Disks (RAID), optical storage devices, magnetic storage devices, electrical storage devices and a combination thereof.

12. The system defined in claim 4 further comprising software executing on the institution server for updating the index.

13. The system defined in claim 12 further comprising software executing on the institution server for calculating a period of time since the last access to the stored data and images and deleting the data and images from the institution RAM and database if the calculated period exceeds a reference period.

14. The system defined in claim 12 further comprising software executing on the institution server for continuously calculating the capacity of the institution database and deleting the oldest stored images if the measured capacity is less than a reference capacity of the RAM and database of the institution server.

15. The system defined in claim 1 further comprising software executing on the institution server for transmitting the information received from the institution network to the central server through the communication link.

16. The system defined in claim 1 wherein the communication link is selected from the group consisting of wire links, the Internet, dedicated lines, and Virtual Private Network (VPN), and wireless links and a combination thereof.

17. The system defined in claim 6 further comprising software executing on the central server for calculating a decision as to a type of the request received from the institution server through the communication link between the institution and central servers.

18. The system defined in claim 17 further comprising software executing on the central server for directing the determined request based on the decision of whether the transmitted request is for storage, retrieval or query for information and the delivery instructions associated with the determined request.

19. The system defined in claim 18 further comprising software executing on the central server for verifying the institution identifier in response to the request for storage of transmitted information, and software executing on the central server for terminating the transaction if the institution identifier is not verified.

20. The system defined in claim 19 further comprising software executing on the central server for searching the requested information.

21. The system defined in claim 20 further comprising software executing on the central server for saving at least one copy of the information associated with the storage request.

22. The system defined in claim 21 further comprising software executing on the central server for generating a request to specify whether the request is to be stored or transmitted to a receiver which is selected from the group consisting of the institution server and institution network, and software for receiving a response from a sender.

23. The system defined in claim 21 further comprising software executing on the central server for identifying information contained in the storage request, and software for searching for the copy of the requested information.

24. The system defined in claim 21 further comprising software executing on the central server for generating a notice acknowledging the received response from a sender.

25. The system defined in claim 19 further comprising software executing on the central server for indexing the information associated with the validated storage request.

26. The system defined in claim 25 wherein the central server includes warehouse RAM and warehouse database, the system further comprising software executing on the central server for storing the data in the central server based on specific instructions of the central server.

27. The system defined in claim 26 further comprising software executing on the central server for examining the state of the warehouse RAM and database, and manipulating the stored information based on the specific instructions of the central server.

28. The system defined in claim 26 further comprising software executing on the central server for generating a notice informing a sender of the storing of the information in the central server.

29. The system defined in claim 26 further comprising software executing on the central server for verifying the institution identifier in response to the request selected from group consisting of the request for query, which comprises verification of the storage of specified information, and the request for retrieval of information.

30. The system defined in claim 29 further comprising software executing on the central server for searching the warehouse RAM and database and the central database in response to the request for query and the request for retrieval of information and transmitting the searched information to the institution server.

31. The system defined in claim 30 further comprising software executing on the central server for generating transaction acknowledgement, institution and patient identifiers and the account number transmitted along with the searched information in response to the request for retrieval of data and images.

32. The system defined in claim 17 further comprising software executing on the central server for decompressing and decrypting the information transmitted from the institution server.

33. The system defined in claim 17 wherein the central server has a transmitter for transmitting the information associated with the request for storage to the institution database.

34. The system defined in claim 33 further comprising software executing on the central server for periodically monitoring the information stored on the central database to verify the stored data integrity.

35. The system defined in claim 34 further comprising software executing on the central server for periodically generating reports on the monitoring results for historical reference.

36. The system defined in claim 31 further comprising an account and billing database in communication with the central server, and software executed on the central server for transmitting the account information associated with each of the requests to the account and billing database.

37. The system defined in claim 36 further comprising software executed on the central server for periodically generating invoices detailing the number of requests made by the institution network and processed by the central server, and software executed on the central database for transmitting the invoices to the institution network.

38. The system defined in claim 1 wherein the central database is a computer server having a storage selected from the group consisting of RAID, jukebox containing a plurality of optical disks and their magnetic equivalents configured to operate as a long-term-permanent storage device, electrical storages and a combination thereof for the categorized delivery instructions received from the central server.

39. The system defined in claim 30 further comprising software executing on the institution server for restoring the information associated with the response transmitted from the central server to the institution network.

40. The system defined in claim 2 further comprising software executing on the institution server for generating a message to the institution network verifying the receipt of the information.

41. The system defined in claim 3 further comprising software executing on the institution server for searching the index.

42. A system for communication, storage, retrieval and delivery of information comprising:
   a plurality of institution servers, each having a respective random access memory (RAM);
   a respective institution database accessible by said institution server;
   software executing on each of said institution servers for receiving information from a respective healthcare institution;
   software executing on each of said institution servers for selectively storing the information in a storage selected from the group consisting of said database and RAM and a combination thereof;
   software executing on each of said institution servers for generating a respective index based upon the received information, and for storing the index;
   software executing on each of the institution servers for continuously calculating the capacity of the RAM and database and for comparing the calculated capacity with a reference value;
   software executing on each of the institution servers for automatically updating the index by controllably deleting the information based on a set of specific instructions of the institution server after the calculated capacity is at least equal to the reference value;
   a central server;
   a primary long-term central database accessible by said central server;
   a communication link between said central and the plurality of institution servers;
   software executing on said central server for receiving the information from said institution servers through the communication link;
   software executing on the central server for storing the received information on said central database;
   software executing on said institution server for automatically searching the index in response to a query;
   software executing on said warehouse server for searching the warehouse server if the information has not been found on the institution server or the institution database, and for transmitting the information to the institution server for storage thereon in response to the query; and software executing on said institution server for temporarily storing on the institution server and institution database, based upon various selected criteria, the retrieved information in anticipation of near future use by the institution.

43. The system defined in claim 42 further comprising software executed on each of the institution servers for directly communicating with the other institution servers through respective communication links, each of the communication links between the institution servers and between each of the institution servers and the central server being selected from the group consisting of the Internet connection, dedicated lines, and Virtual Private Network (VPN) and a combination thereof.

44. The system defined in claim 42 further comprising software executing on each of the institution servers for automatically storing the information upon receiving the requested information from the central database.

45. The system defined in claim 42 further comprising software executing on the central server for periodically monitoring the stored information on the central database.

46. The system defined in claim 42 further comprising at least one redundant central database accessible by the server and receiving at least one copy of the information stored in the primary central database.

47. The system defined in claim 42 wherein the central database includes a magnetically operated storage selected from the group consisting of RAID, at least one jukebox containing a plurality of optical disks and their magnetic equivalents, an electrical storage and a combination thereof.

48. The system defined in claim 42 further comprising software executing on each of the institution and central servers for periodically verifying the integrity of the stored information by using the calculated digital signature associated with the scanned information.

49. A method for communication, storage, retrieval and delivery of information between the system and participating healthcare institution and sites comprising:

(a) transmitting information from an institution network to an institution server;

(b) generating an index based on the transmitted information and storing the index in an institution storage device selected from the group consisting of RAM and database and a combination thereof;

(c) calculating the capacity of the RAM and database to selectively delete the information upon reaching a predetermined capacity after the transmitted information has been received from the institution network;

(d) encrypting the information for further transmission thereof from the institution server to a central server via a communication link;

(e) decrypting and storing the decrypted received information in RAM and database of the central server, respectively;

(f) transmitting the stored information to at least one long-term central database for storing; and (g) continuously repeating steps (a) through (f).

50. The method defined in claim 49 wherein the step of transmitting data from the institution network includes a step of transmitting a request selected from the group consisting of query request, storage request, retrieval request and a combination thereof and delivery instructions associated with each of the requests.

51. A method defined in claim 50 further comprising the step of transmitting an institution identifier and a patient identifier with each of the requests.

52. The method defined in claim 49 wherein the step of encrypting includes application of a digital signature to the information for verifying integrity of information received from the institution network.

53. The method defined in claim 52 further comprising the step of digitally signing and, selectively and losslessly compressing a system header, a DICOM meta header, or a DICOM header upon receiving the information from the institution network.

54. The method defined in claim 53 further comprising the step of applying a message signature trailer to the compressed information.

55. The method defined in claim 49 further comprising the step of selectively re-encrypting the transmitted information.

56. The method defined in claim 55 further comprising the step for determining the request for query, which comprises verification of the storage of specified information, the request for retrieval of data and images and the request for storage.

57. The method defied in claim 56 further comprising the step of searching the central server RAM and RAID and the central database in response to the request for query and the request for retrieval of information and the step of transmitting the searched information to the institution server.

58. The method defined in claim 57 further comprising the step of re-storing the information received from the central server in the RAM and database of the institution server.

59. The method defined in claim system defined in claim 50 further comprising the step of generating transaction acknowledgement including the institution and patient identifiers and the account number transmitted along with the searched information in response to each of the requests.

60. The method defined in claim 49 further comprising the step of periodically monitoring the information stored on the central database to verify the stored data integrity.

61. The method defied in claim 59 further comprising the step of periodically generating reports on the monitoring results for historical reference.

62. The method defined in claim 49 further comprising the step of storing account and billing information accompanied the delivery instruction in an account and billing database.

63. The method defined in claim 62 further comprising step of periodically generating invoices detailing the number of requests made by the institution network and processed by the central server, and the step of transmitting the invoices to the institution network.

64. The method defined in claim 49 further comprising the step of periodically identifying the information stored in the central database needed to be transferred to the institution server in accordance with a system of requirements generated by the institution network without the request in anticipation of near future use by the institution.

65. A data and image storage and retrieval system for medicinal institutions comprising:

a warehouse server;

at least one warehouse database accessible by said warehouse server;

a proxy server for receiving data and images;

at least one proxy database accessible by said proxy server;

at least one terminal for inputting data and images into the system;

a communications link connecting said at least one terminal to said proxy server, and said proxy server to said warehouse server;

software executing on said at least one terminal for transmitting the inputted data and images to said proxy server;

software executing on said proxy server for receiving and temporarily storing the inputted data and images, and for generating an index based upon the received inputted data and images;

software executing on said proxy server for automatically moving, based upon various selected criteria, the inputted data and images to the warehouse server;

software executing on said warehouse server for receiving and storing the moved data and images;

software executing on said at least one terminal for generating a query for information based upon an inputted request;

software executing on said proxy server for automatically searching the index in response to the query, and for searching the warehouse server if the information has not been found on the proxy server or the at least one proxy database;

software executing on said warehouse server for transmitting the information to the proxy server for storage thereon in response to the query;

software executing on said proxy server for temporarily storing, based upon various selected criteria, the retrieved information in anticipation of near future use by the institution.

* * * * *

UNITED STATES PATENT AND TRADEMARK OFFICE
CERTIFICATE OF CORRECTION

PATENT NO.        : 6,574,742 B1                                             Page 1 of 1
APPLICATION NO.   : 09/711052
DATED             : June 3, 2003
INVENTOR(S)       : David Jamroga et al.

It is certified that error appears in the above-identified patent and that said Letters Patent is hereby corrected as shown below:

Col. 21, lines 60-61:

"and g) continuously repeating steps (a) through (f)" should be deleted and read
--(g) inputting a query for information onto the institution network and transmitting the query to the institution server;
   (h) searching the institution server and if not found, searching the central database for the information; and
   (i) transmitting the information from the central database to the institution server for temporary storage thereon based upon various selected criteria, in anticipation of near future use by the institution--.

Signed and Sealed this

Second Day of January, 2007

JON W. DUDAS
*Director of the United States Patent and Trademark Office*